United States Patent [19]

Moberg

[11] Patent Number: 5,525,635
[45] Date of Patent: Jun. 11, 1996

[54] PHARMACEUTICAL COMPOSITIONS CONTAINING PROPYLENE GLYCOL AND/OR POLYETHYLENE GLYCOL AND UREA AS ACTIVE MAIN COMPONENTS AND USE THEREOF

[76] Inventor: Sven Moberg, P.O. Box 2057, S-433 02 Partille, Sweden

[21] Appl. No.: 150,245

[22] Filed: Nov. 9, 1993

Related U.S. Application Data

[63] Continuation of Ser. No. 964,104, Oct. 8, 1992, abandoned, which is a continuation of Ser. No. 590,432, Sep. 27, 1990, abandoned, which is a continuation of Ser. No. 230,375, filed as PCT/SE87/00053, Feb. 04, 1987 published as WO87/04617, Aug. 13, 1987, abandoned.

[30] Foreign Application Priority Data

Feb. 4, 1986 [SE] Sweden .................. 8600501

[51] Int. Cl.⁶ .................. A61K 31/17; A61K 31/19; A61K 31/045
[52] U.S. Cl. .................. 514/588; 514/557; 514/738
[58] Field of Search .................. 514/557, 588, 514/738

[56] References Cited

U.S. PATENT DOCUMENTS

| | | | |
|---|---|---|---|
| 3,395,236 | 7/1968 | White | 514/21 |
| 3,666,863 | 5/1972 | Swanbeck | 424/316 |

FOREIGN PATENT DOCUMENTS

| | | |
|---|---|---|
| 0138029 | 4/1985 | European Pat. Off. . |
| 1911144 | 9/1970 | Germany . |
| 2608221 | 7/1977 | Germany . |
| 2086223 | 5/1982 | United Kingdom . |
| 2116425 | 9/1983 | United Kingdom . |

OTHER PUBLICATIONS

Patent Abstracts of Japan, abstract of JP Kokai No. 52–87235, published 20 Jul. 1977.
Karnan, vol. 9, No. 1, issued 1985 (AB Leo, Helsingborg, Sweden), J. Faergemann, "Pityriasis versicolor, Orsak, diagnos och behandling", see pp. 13–17, especially p. 13, left column, third paragraph and p. 17, left column, second paragraph.
Zaias Onychomycosis. Arch Derm. 1972; 105: 263–74.
Ishii M. Hamada I, Asai Y. Treatment of onychomycosis by ODT therapy with 20% urea ointment and 2% tolnaftate ointment. Dermatologica 1983; 167: 273–9.
Priestley G. C. Savin J. A. The microbiology of dandruff. Br J Dermatol 1976; 94: 469–71.
Shuster S. The aetiology of dandruff and the mode of action of therapeutic agents. Br J. Dermatol 1984; III: 235–42.
Nielson P. G. The importance of the vehicle in the treatment of dermatophytosis in hereditary palmo-planter keratoderma. Mykosen 1984; 27 (5):227–30.
Gamborg Nielsen P. Dermatophyte infections in hereditary palmo-plantar keratoderma. Dermatologica 1984; 168: 238–41.
Faergemann J. Fredriksson I. Propylene glycol in the tretment of tinea versicolar. Acta Derm Venereol 1979; 60:92–3.
Faergemann J. Bernader S. The activity in vitro of five different anti-mycotics against pityrosporum orbiculare. Acta Derm Venereol 1979; 59: 521–4.
Leyden J. J. Stewart R, Kligman A. M. Updated in vivo methods of evaluating topical antimicrobial agents on human skin. J. Invest Dermatol 1979; 72: 165–70.
Martindale, The extra pharmacopoeia, Ed. 28, 1982.
Bagatell F. K. Topical therapy for onychomycosis. Arch Derm 1977; 113: 378.
Ashton H. Frenk E, Stevenson C. J. Urea as a topical agent. Br. J. Dermatol 1970; 84: 194–6.
Farber E. M., South D. A. Urea ointment in the nonsurgical avulsion of nail dystrophies. Cutis 1978; 22: 689–92.
South D. A., Farber E. M. Urea ointment in the nonsurgical avulsion of nail dystrophies.—a reappraisal. Cutis 1980 25: 609–12.
Nolting S. Non-traumatic removal of the nail and simultaneous treatment of onychomycosis. Dermatologica 1984; 169 (suppl. 1): 117–20.
English language abstract of German Patent DE 2608221, 1977.

*Primary Examiner*—Raymond Henley, III
*Assistant Examiner*—William R. A. Jarvis
*Attorney, Agent, or Firm*—Browdy and Neimark

[57] ABSTRACT

Composition active for the treatment of hyperkeratotic skin diseases, seborrheic eczema, dermatomycosis and onychomycosis, thickened skin and chapped skin, containing propylene glycol and/or polyethylene glycol and urea as active main components and optionally other active substances and additives, which composition is characterized in that it contains 40–80% by weight propylene glycol and/or polyethylene glycol, 5–20% by weight urea and 0–55% by weight of other active substances and/or additives; as well as the use thereof.

12 Claims, 11 Drawing Sheets

PHARMACEUTICAL COMPOSITIONS CONTAINING PROPYLENE GLYCOL AND/OR POLYETHYLENE GLYCOL AND UREA AS ACTIVE MAIN COMPONENTS AND USE THEREOF

This application is a continuation of application Ser. No. 07/964,704, filed Oct. 8, 1992, now abandoned, which is a continuation of application Ser. No. 07/590,432, filed Sep. 27, 1990, now abandoned, which is a continuation of application of Ser. No. 07/230,375 filed as PCT/SE87/00053, Feb. 04, 1987 published as WO87/04617, Aug. 13, 1987, now abandoned.

FIELD OF THE INVENTION

The present invention is relating to compositions for the treatment of hyperkeratotic skin diseases, seborrheic eczema (mainly of the scalp), mycosis of the skin and nails as well as thickened and chapped skin (rhagades).

The composition consists of a mixture of propylene glycol (optionally polyethylene glycol) and urea as pharmacologically active main components, optionally in combination with lactic acid for the treatment of nails and skin and with the further addition of glycerol and gel forming agents for the treatment of skin as well as alcohol for the treatment of the scalp.

Propylene glycol is preferably used in concentrations between 40 and 80 percent by weight, urea in concentrations between 5 and 20 percent by weight and lactic acid in amounts up to 20 percent by weight, glycerol up to 10 percent by weight, gel forming agents up to 5 percent by weight as well as alcohol up to 55 percent by weight.

BACKGROUND OF THE INVENTION

It is previously known that propylene glycol is a favorable solvent and penetration promoting agent for other pharmacologically active substances. It is further a very common solvent and is used in several drugs above all in local preparations. Since propylene glycol is a common solvent it can also be used to dissolve urea (UA-A 3 395 236 and GB-A 2 116 425, DE-B 1911144 and DE-A 2847975 and FI-B 56486). For this purpose propylene glycol is preferably used in concentrations under 10%, very occasionally up to 40%, when e.g. propylene glycol is included in combination with fatty acids and about 0.02% urea (US-A 3 395 236). Propylene glycol has also been shown to be effective against one type of yeast fungi, Pityrosporum orbiculare, giving a specific skin disease Pityriasis versicolor. An aqueous solution of 50% propylene glycol has been shown to give certain results.

SUMMARY OF THE INVENTION

In the present invention, by using propylene glycol in high concentrations (over 40%), in combination with urea and optionally lactic acid, the unique more potent inherent effects of the combinations are used against mycosis of the nails and dermatophytosis as well as hyperkeratotic skin diseases and seborrheic eczema and also thickened and chapped skin.

DETAILED DESCRIPTION OF THE INVENTION

Propylene glycol

Propylene glycol is a water soluble, odorless, colorless, atoxic solvent, which is used as vehicle in several local and peroral preparations. The agent is also given in the form of injections. Characterizing features for propylene glycol are i.a. its slightly keratolytic (cornea dissolving) and water binding properties. The agent has also an antimycotic and antibacterial effect, (5, 6, 7, 8, 9, 10).

In some cases a local irritating effect has been reported as a side effect (6) with an increased concentration of the solvent. Also allergic reactions are reported occasionally (10).

The agent is also test-wise used on larger skin areas in connection with yeast fungi infections (pityriasis versicolor) with favorable results (7). It is shown to potentiate the effect of other simultaneously added drugs, (5, 6), in connection with dermatomycosis but separately it has a weaker effect, (6). This applies also when treating nails (11).

The concentration of propylene glycol is, however, low when used in local preparations. Propylene glycol is then included in order to dissolve other substances. The penetration promoting properties thereof are utilized in combination with other potent substances, e.g. steroids. Thus, several steroid preparations for local application contain propylene glycol.

The potent keratolytic and fungicidal properties which, i.a. are characterizing the invention are obtained with propylene glycol in a high concentration of about 70%:

a) in combination with urea, lactic acid and glycerol as well as gel forming agents for the treatment of hyperkeratotic skin diseases, and b) in combination with urea and lactic acid for the treatment of mycosis of the nails.

Thus, propylene glycol is included in the claimed preparation as active substance in combination with other active substances (e.g. urea, lactic acid) and not only as a solvent thereof.

Urea

Urea is a reliable atoxic water soluble substance for the treatment of skin and scalp. Urea is i.a. included in Calmuril and HTH®.The Calmuril solution is registered with the indication seborrheic eczema. Urea has an antibacterial, antimycotic, protein-dissolving, keratolytic, water binding and anti-pruritic effect, (11, 13, 14) and has also penetration promoting properties and a low pH-value (15, 2). Urea in 20 to 40% has a nail dissolving effect under occlusion, (13, 1). According to the method as hitherto used, the nail is covered with a paste of urea under occulsion during one week. (13). Said method requires a skilled staff. Side effects reported from the use of urea are i.a. a temporary stinging effect.

Urea may also be included in combination with substances with an antimycotic effect. An antimycotic agent (bifonazol) Mycosporan® is presently tested in combination with urea for the treatment of mycosis of the nails (Dermatologica 169; suppl. 1, pp. 117–120 (1984)).

Acidum lacticum (lactic acid)

Lactic acid has i.a. an acidifying effect.

Example

| Preparation | | | Control treatment: | |
|---|---|---|---|---|
| I. | Urea | 20% | Lactic acid | 10% |
| | Lactic acid | 10% | Propylene glycol | 90% |
| | Propylene glycol | 70% | | |
| II. | Urea | 20% | | |
| | Propylene glycol | 80% | | |

-continued

| Preparation | | |
|---|---|---|
| III. | Urea | 20% |
| | Propylene glycol | 40% |
| | Alcohol (70%) | 40% |
| IV. | Urea | 20% |
| | Propylene glycol | 40% |
| | Lactic acid | 10% |
| | Alcohol (70%) | 30% |
| Preparation*) | | |
| V. | Urea | 15% |
| | Lactic acid | 10% |
| | Glycerol | 5% |
| | Propylene glycol | 70% |

Preparations I and II were used for the treatment of mycosis of the nails, preparation III and IV for the treatment of seborrheic eczema on the scalp and preparation V for treatment of the skin.

The mutual proportional ratios between the substances as stated above are not absolute but can be varied within the limits as stated in the claims and the preparations can be used without limitation for all of the indications as stated even if the test is performed on specific indications.

*) To the preparation for skin treatment a gel forming agent was added in an amount of 0.5–5, preferably 0.5–3% by weight, in order to obtain a better consistency. E.g. klucel, Carbomer 940 or Macrogol 6000 or optionally other gel forming agents can be used.

A composition containing urea and propylene glycol for the treatment of nail fungus.

Mycosis of the nails is a common complaint, which gives stained, sometimes thickened fragmented nails. Nails can be infected by dermatophytes, yeast fungi, mould, but also bacteria may be contributory (1).

Preparations recorded for the treatment of mycosis of the nails by local application are imidazole derivatives, e.g. Canesten®, Pevaryl®, Daktar® and previously also a combination preparation Onycho-Phytex, which, however, has a comparatively bad healing effect.

The percentage of healing as obtained by a griseofulvin (Fulcin®) is low despite a long time of treatment (2). Further, the agent is only effective against dermatophytes and it lacks effect against yeasts, mould and bacteria.

Neither is the currently registered drug ketaconazole (Fungoral®) suitable for the treatment of mycosis of the nails separately due to the side effects of the preparation.

It is a well known fact that mycosis of the nails and especially toe nails as attacked are more difficult to treat than many other forms of mycotic infections. Inferior results are, as mentioned, obtained by local as well as peroral treatment. The period of treatment is calculated to be between 6 and 12 months. Local preparations for mycosis of the nails is furthermore badly documented. Doctors currently advise patients to refrain from treatment of toe nails due to the bad results of treatment.

Review of clinical investigations

The investigation was performed double blind after randomising by comparison of two solutions, one containing a combination of 20% urea, 10% lactic acid and 70% propylene glycol (solution A) (example I) and the other containing propylene glycol 90% in combination with lactic acid 10% (solution B) (control).

Urea is well soluble at a concentration of 10–20% in propylene glycol. By the addition of lactic acid an increased acidity is obtained, which is favorable since a low pH-value inhibits the growth of the fungi in the nail.

Liquid preparations were added in the form of drops and penetrated in that form into the nail substance. The treatment was cosmetically well accepted.

The low effect of many now recorded nail treatment agents probably is due to that the substances do not effectively penetrate the nail attacked by fungi. An increased penetration of the nail substance is obtained by the new composition of urea, propylene glycol and lactic acid. The antimycotic effect might be enhanced by the addition of other pharmacologic active substances.

Twenty-one (21) patients with chronic mycosis of the nails participated in a clinical test. 68 nails infected by fungi were treated (58 toe nails and 10 finger nails). Culturing before the treatment showed in each case growth of Trichophyton fubrum attacking the nails. All of the nails were badly attacked by fungi with thickened nails, discoloration, onycholysis (discharge of the nail plate) and part fragmentation of the nail plate.

The nails were divided into two groups:
Group A obtained solution A (urea, propylene glycol as main substances)
Group B obtained solution B (propylene glycol as main substance).

The duration of the complaint (average value) was 3 years and 10 months (1–10 years).

Treatments were previously performed locally with imidazole-solutions (Pevaryl or Canesten) on average during 6 months (1–24 months). Only 3 of 21 patients stated improved results, 4 of 21 stated that the nails had become softer, 1 of 21 stated a deterioration and 13 of 21 considered the previous treatment to be without effect. Said patients were, in view thereof, motivated for new treatment.

The nail area as attacked was on average 88% (group A) and 81% (group B) respectively, before the treatment with the claimed drug. The solutions were dropwise applied to the nails (2–5 drops per nail) once daily. During the first month the nail plate was also covered with skin tolerant plaster after each application of the nail agent.

Results

The results were documented by photos before and during the treatment (after 14 days and then once per month) and according to record.

Already after 14 days an obvious improvement was recorded. The nail plate was, furthermore, softer in group A (urea-propylene glycol) than in group B (propylene glycol). Parts of the nails as attacked were in group A almost dissolved The result was recorded as percent of the nail area cured after one and two months respectively (mean values):

| | 1 month | 2 months |
|---|---|---|
| Solution A (urea-propylene glycol): | 48% | 59% |
| Solution B (propylene glycol): | 22% | 39% |

$\geq$80% of clean nail area was recorded after treatment for two months for 53% (16 of 30) of the nails in group A and for 26% (10 of 38) of the nails in group B.

$\geq$90% of clean nail area was recorded after the same treatment period for 30% (9 of 30) of the nails in group A and for 5% (2 of 38) of the nails in group B. One nail (group A) was healed altogether during this period.

Thus, urea-propylene glycol gave a significantly better effect than only propylene glycol. The softening effect was, furthermore, more pronounced with urea-propylene glycol.

A follow-up after terminated treatment will be made later on. Since the treatment period for nails is calculated to be at least 6 months, a continued treatment can be expected to give a better treatment result. Complete healing of the nail plate cannot always be expected due to matrix-damage caused by the mycotic infection (14).

Side effects

Two patients recorded a slight stinging effect and tenderness around the nail during one day. Three patients stated a slight redness of the skin around the nail during one to three days. One patient observed also desquamation of the skin around the nail.

Conclusion

By combining 20% of urea with highly concentrated propylene glycol (70%) and lactic acid (10%) a new and previously untested composition for the treatment of onycho mycosis is obtained, which has entailed unexpected and good results. It is further shown that the combination is more effective and has a better softening and more potent keratolytical (cornea disintegrating effect) than propylene glycol alone. By a combination of propylene glycol and urea a penetrating effect furthermore is obtained, which can be promoted by occlusion of skin tolerant plaster around the nail. The combination of propylene glycol and urea is believed to be a solvent which promotes the penetration of other substances having antimycotic effect. As a comparison it can be mentioned that it is commonly known among men skilled in the art, by support of investigations, that preparations solely containing urea have a very low effect on mycosis of the nails.

Nail lesions from other causes

Chronic onychia with impressions in the nail plate can be improved and debris under psoriasis nails can be removed with a solution of urea-propylene glycol at the same concentration (cf. pictures). compositions containing urea and propylene glycol with the addition of glycerol and acidum lacticum (lactic acid) for the treatment of skin diseases characterized by hyperkeratosis and scaling A potent keratolytic and softening effect superior to other commercial preparations or extempore preparations containing e.g. urea or salicylic acid is achieved by a combination of urea with propylene glycol at high concentration. The softening properties are enhanced by the addition of glycerol and lactic acid. The preparation also obstructs the reddening of the skin (e.g. by psoriasis) and has a curative effect also on inflammatory (erythematous) forms of eczema, which seems paradoxical in view of the often irritating effect of propylene glycol at high concentrations. The substances as included are each known and reliable. The novelty lies in 1) the composition of the preparation which gives
a) an unexpected good effect from the treatment,
b) pharmaceutical properties where certain particulars are concerned with the solubility of the substances and so on. Also 2) the indications of the claimed composition are new (cf. the report of the result). The combination of the substances as included should, theoretically, have an effect on hyperkeratotic skin diseases and scaling skin diseases by the properties of the substances known per se. However, the rapidly occurring high effect was quite unexpected and might be explained by a synergistic effect between the included substances, these substances being well balanced in relation to each other.

Urea has at a concentration of 10–20% shown good solubility in propylene glycol. An enhanced acidifying effect, desired in local skin preparations, is obtained by the addition of lactic acid.

Advantages obtained with the claimed preparation in the treatment of hyperkeratotic skin diseases 1. The preparation is cosmetically attractive, since it does not smear or soil, is odorless, penetrates the skin easily and has a low pH-value, which is favorable.
2. The substances as included are acceptable to the skin and give rare side effects (cf. under the title Side effects).
3. The preparation is an alternative for the patients who desire cortisone-free treatment since the preparation lacks the side effects with i.a. skin atrophy (attentuation) (valid mainly for group III–IV steroids) obtained by cortisone.
4. The preparation is easy to manufacture, the raw materials are relatively cheap (cf. under the title Manufacturing process).
5. The preparation is long-lasting without the addition of preservatives (cf. under the title Stability test. This test relates to an analysis where the concentration of urea was unchanged after a shelf-life of three months).
6. The preparation has antibacterial and antimycotical properties.
7. Other substances can also be combined with the composition such as e.g. Hydrocortisone, or fluorinated corticosteroides in an amount of up to 2%, antimycotical substances such as e.g. imidazole derivatives in amounts up to 2%, collodium 1–10%, salicylic acid 1–10%, vitamin A 0–1%, vitamin A-acid 0–1% (weight) and derivatives thereof, which give several advantages i.a. by increasing the penetration properties of the steroid.
8. One advantage with the preparations according to the present invention is that in addition to being pharmaceutically active in the amounts as defined herein, they also can act as solvents for other pharmaceutically active substances such as e.g. the substances stated above.

A report of the results of treatment of chronic hyperkeratotic skin diseases

Examples of diseases that can be treated are:
psoriasis
pustulosis palmoplantaris
tylotic eczema
hyperkeratotic eczema
neurodermatitis
ichthyosis
keratodermia
mycotic infections
clavi (corns)

In total 40 patients are presently being treated.

Symmetrically located similar skin lesions were chosen for the treatment. One side was treated with the composition of the present invention consisting of urea-propylene glycol, lactic acid, glycerol and a gel forming agent (example V), and the other side with a potent corticosteroid (group III) and a known softening preparation containing salicylic acid 2–5% or urea 10% (control side).

Results

The preliminary results, which were documented by photos, were so favorable that conclusions with respect to the effect of the treatment could be drawn already at an early stage. The effect of the claimed composition was unexpected and in some cases almost dramatic. A potent desquamation of the skin gave in all cases, often already after 14 days, a remarkable improvement and in certain cases a complete cure after a treatment of one month. The effect was more rapid and better than that obtained by the control treatment. The treatment of hyperkeratotic eczema, chronic mycotic infections and psoriasis gave the best results. Said complaints were reported separately. The preparation has also an excellent effect on dry skin and chaps.

Side effects: a slight stinging effect was noted in individual cases.

A. Hyperkeratotic eczema

These are characterized by thickened, scaling skin often with chaps (rhagades). Eczema on the palms of hands and the soles of feet was treated.

Results

Very favorable results with a rapid, one-sided peeling effect and a remarkable improvement in the curing of the eczema were noted for the preparation of the present invention. Remarkably, also painful, deep rhagades [chaps] were cured and the pain disappeared. The curing period was on average about one month. The control side showed inferior results.

B. Chronic mycotic infections

Mycotic infections caused by a dermatophyte, commonly Trichophyton rubrum. The symptoms are often a dry chapping in the palms of the hands and the soles of the feet. The infections are, as a rule, chronic, and therefore difficult to treat and frequently recurrent.

Results

Remarkably good results with rapid desquamation and apparently healed skin after about one months treatment is achieved with the preparation of the present invention. The combination of rapid repellation of infected skin cells, the antimycotic effect of the preparation as well as its low pH-value probably contribute to the effect. These three properties are achieved by the well balanced exact composition of the preparation. These properties together make the preparation new in relation to other reliable antimycotical agents. No stinging effect was noted during treatment of the palms of the hands and the soles of the feet, which, however, might be a problem if the agent is used on discharging or reddening skin areas or in groins. Other methods of treatments are presently recommended in this respect. Thus, the main indication for treatment of dermatomycosis is a chronic infection in the palms of the hands and the soles of the feet or dry, scaling mycotic attacks on smooth skin.

Pityriasis versicolor

Caused by a yeast fungus, Pityrosporon orbiculare, which also can be treated with the preparation according to the invention. The treatment of this complaint has been tested previously with 50% propylene glycol in water solution, and thus, is previously known (7).

Conclusion

Novelty: the composition of the claimed preparation with the indication dry eczema and mycotic infections (dermatophytosis). The invention is not obvious in view of the unexpected favorable effect of the product.

C. Psoriasis

Psoriasis is a skin disease, characterized by reddened, flaking skin lesions. The disease has, as a rule, a chronic course. Local agents for the treatment of psoriasis are often smeary and discoloring e.g. dithranol or tar. Steroid preparations are cosmetically attractive but can give the side effects of cortisone in the form of i.a. skin-attenuation. Softening preparations containing e.g. salicylic acid and urea in a cream or ointment base have a certain peeling effect but are not separately sufficiently active. A cosmetically acceptable local agent having a more potent effect and lacking the side effects of cortisone for the treatment of psoriasis is presently not available.

Symmetrically situated, well defined chronic psoriasis lesions were chosen for the treatment in order to more critically evaluate the effect of the claimed preparation. One side was treated twice a day with the claimed preparation and the other side obtained common softening treatment and a potent steroid ointment (group III), the last mentioned group twice a day.

Result

The result of the treatment was totally unexpected. A very rapidly occurring effect with a pronounced recovery was noted already after fourteen days of treatment with the claimed preparation. A treatment period of one month resulted in many cases in a complete healing of the area as treated. The effect was comparable, or better than that obtained on the control side which was treated with a potent (group III) steroid. In addition to a keratolytic effect, it was also noted that the erythema receded. This anti-psoriatic effect is difficult to explain in the light of the present knowledge about the separate components as included. This components might have a synergistic effect and might also simultaneously have an anti-inflammatory or anti-mitotic effect.

Side effects

A slight stinging effect was noted in some cases (common for urea). The patient considered the cosmetic properties of the preparation to be very favorable (cf. page 11). The properties of the preparation which bring about rapid desquamation are also very important e.g. in combination with treatment with light.

Conclusion

The indication for the composition is new. The result of the treatment was very favorable with an unexpected, rapid keratolytic and anti-psoriatic effect comparable with potent corticosteroids and more effective than common softening treatment of the type shown by urea in a cream base.

The preparation according to the invention provides a very valuable addition to the treatment armoury for psoriasis patients since it is cosmetically attractive and has a good effect.

Further indications:
seborrheic eczema
verrucae

Seborrheic eczema

Seborrheic eczema is a common complaint with itching, erythema and scaling on the scalp. The eczema is often also located on the face, in the armpits and the groin. The hitherto most common methods of treatment have been different steroid-(cortisone)-preparations which have a symptomatic alleviating effect with a temporary itch-relieving and anti-inflammatory effect.

The etiology of seborrheic eczema is commonly discussed and a relatively new hypothesis is that a yeast fungus (Pityrosporon ovale/orbiculare), can be one of the causes thereof (3, 4).

A new method to obtain results of the treatment of seborrheic eczema should be the use of a drug which inhibits the yeast fungus growth and thereby not only gives a symptomatical alleviation but also eliminates the causes thereof. Propylene glycol has such an inhibitory effect.

There is, in view thereof, a common demand for alternative preparations intended for the treatment of seborrheic eczema.

An alternative preparation for the treatment of seborrheic eczema is now obtained by the present invention wherein propylene glycol in mixture with urea is used as an active substance, optionally in combination with other active substances.

Some test cases of seborrheic eczema of the scalp treated with the composition III and IV are reported under the title Example.

The treatment is effective, but the symptoms recidivate after about one to two weeks after the end of the treatment. Two courses of treatment per week are often enough for treatment of maintenance. The solution is in these cases washed out after about five to twelve hours. The preparation for the hair can give a somewhat greasy feeling to the hair and scalp, which however, can be an advantage with dry scalps. The preparation according to the invention is an alternative for the patients who wish to avoid steroid treatment (cortisone preparation) for their eczema. No side effects from the preparation are observed.

Verrucae

A certain effect was also obtained where verrucae was treated with the solution used for mycosis of the nails, which solution contained urea, propylene glycol and lactic acid. The difficulty to force the preparation to remain on the verrucae might be eliminated by e.g. coilodium.

The preparation of the present invention has, by its composition, shown unique properties due to its effect on a great number of skin diseases having different etiology. This is very uncommon in medium. It has further been shown that the combination (urea-propylene glycol) has a more potent keratolytic (cornea disintegrating effect) than propylene glycol separately. The combination is furthermore, effective for nail mycosis.

The skin preparation has, in addition to keratolytic properties, also an anti-psoriatic effect and in some cases also an anti-inflammatory effect. This is surprising and cannot be explained by the mechanisms as regards the effects of each of the separate substances. The combined treatment has also shown a better effect than preparations only containing urea and in many cases also potent corticosteroids (group III).

| Manufacturing example 1: | |
| --- | --- |
| Urea | 20% |
| Lactic acid | 10% |
| Propylene glycol ad. | 100% |

Preparation prescriptions:

The urea is dispersed as finely as possible and mixed with a minor amount of propylene glycol. The remainder of the propylene glycol is then added and all of it stirred together until the urea is dissolved (time consuming). Finally, lactic acid is added.

| Manufacturing example 2: | |
| --- | --- |
| Gel forming agent | 0.5–3% |
| Glycerol 85% | 5% |
| Lactic acid | 10% |
| Urea | 15% |
| Propylene glycol ad. | 100% |

Preparation prescription:

The urea is dispersed as finely as possible and mixed in a minor amount of propylene glycol, whereafter the remainder of the propylene glycol is added and all of it stirred together until the urea has dissolved (time consuming). The glycerol and the lactic acid is added.

A gel forming agent is mixed into a small amount of the above mentioned solution to a homogeneous mixture, whereafter the remainder of the solvent is added and everything is stirred until a homogeneous gel is formed (time consuming).

Stability Test

A stability test was performed by the Central Laboratory of Apoteksbolaget, Solna, on a preparation with the composition:
20% urea
70% propylene glycol
10% lactic acid Analysis after three months of three samples of the preparation wherein the amounts of urea, which is the chemically unstable composition shall be included in an amount of 18–22%. The results as obtained:

| | |
| --- | --- |
| Vial 1. | 20.5% |
| Vial 2. | 19.9% |
| Vial 3. | 19.9% |

Onycho mycosis during 3 years. Treatment with imidazole solution during 1 year without effect.

Figure 1A:
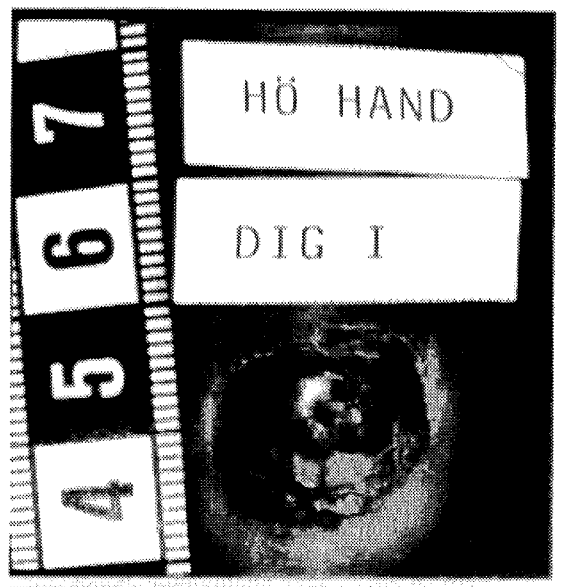
FIGS. 1a–1c Onycho Mycosis

FIG. 1a) Before treatment with the claimed preparation.

Figure 1B:

FIG. 1b) After 14 days of treatment.

Figure 1C:

FIG. 1c) After two months of treatment. The new nail has now started to develop proximally (at the top) and the discolored part is simultaneously successively displaced downwards. This is evident if one compares pictures b and c.

Figure 2A:
Figure 2B:
Figure 2C:

FIGS. 2a–2c Onycho Mycosis

Onycho mycosis during about 3 years. Previous treatment with an imidazole solution made the nails somewhat soft but the patient did not notice any improvement.

FIG. 2a) Before the treatment with the claimed preparation.

FIG. 2b) After 14 days of treatment.

FIG. 2c) After one month of treatment.

Figure 3A:
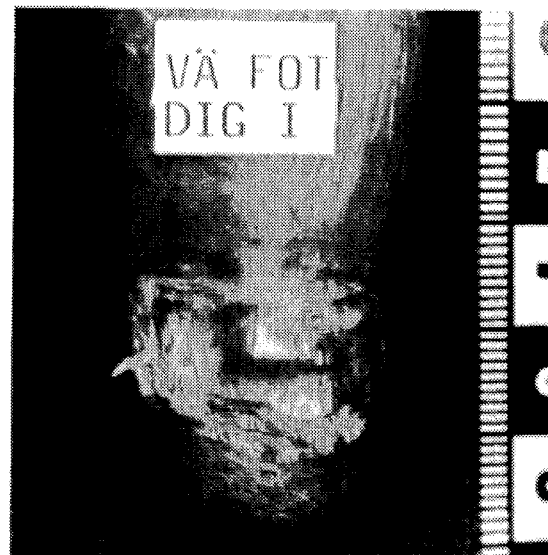
Figure 3B:
Figure 3C:

FIGS. 3a–3c Onycho Mycosis

FIG. 3a) Before treatment with the claimed preparation.

FIG. 3b) Example of the potent nail disintegrating effect of the preparation after one month.

FIG. 3c) After two months. The infected nail substance is displaced and a new nail which cannot be reinfected starts to grow.

Figure 4A:
Figure 4B:
Figure 4C:
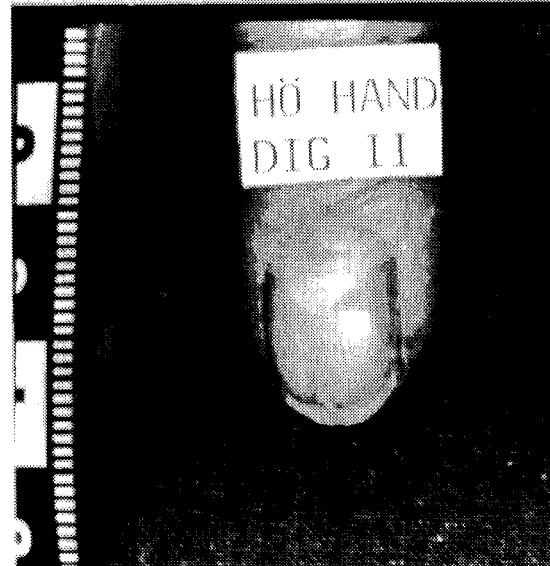

FIGS. 4a–4c

Onychia About 3 years damage of the nail plate. The impression has been newly formed as the nail has grown. Probably matrix damage in connection with hand eczema.

FIG. 4a) Before the treatment with the claimed preparation.

FIG. 4b) Treatment results after 1.5 months.

FIG. 4c) Treatment results after 2.5 months.

Figure 5A:
Figure 5A:
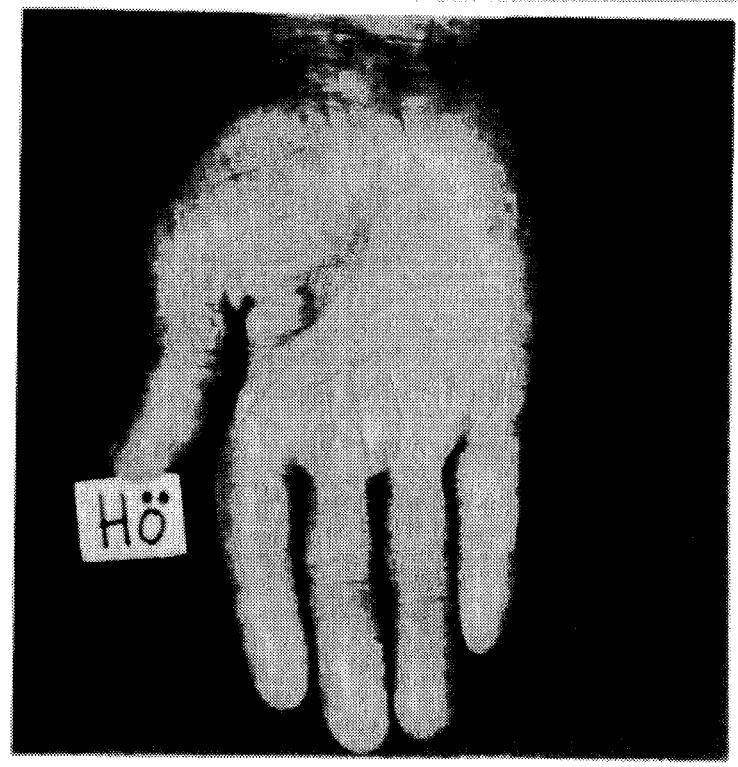
Figure 5B:
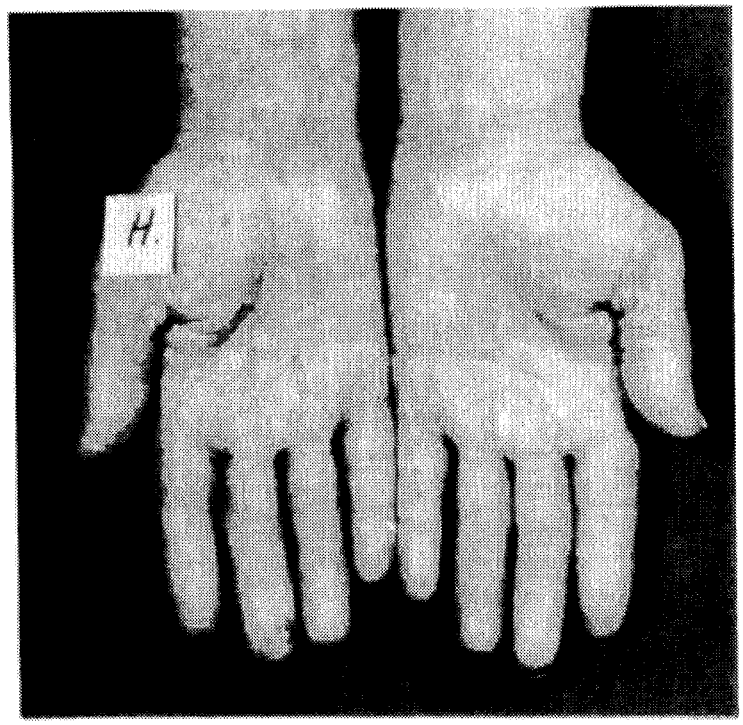
Figure 5B:
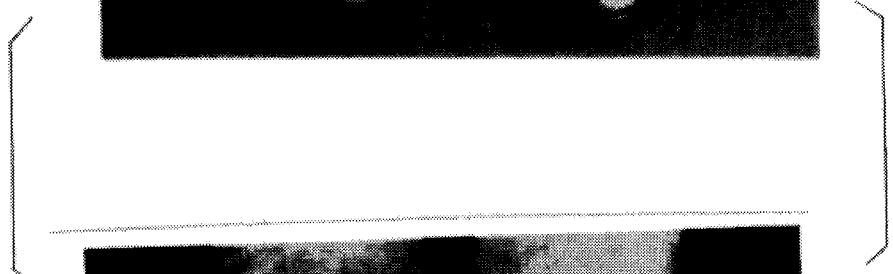
Figure 5B:
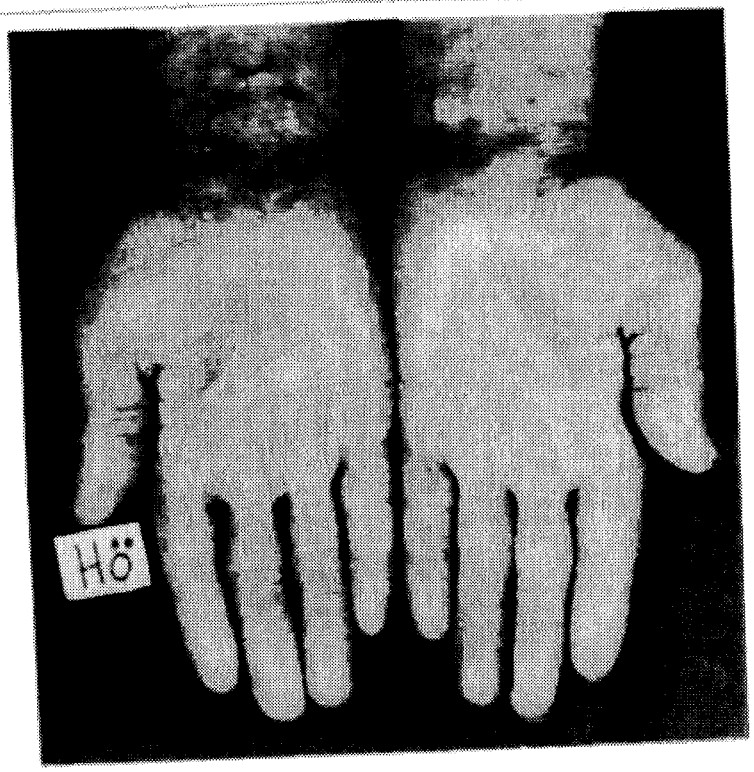

FIGS. 5a–5b

Toxic traumatic iterative hand eczema

Hand eczema since 1969.

Hand eczema before the treatment. The preparation of the present invention was applied to the right hand. (Marked with H).

A potent steroid cream (group III) Celestona valerat was applied to the left hand. The hand eczema was somewhat more pronounced on the right hand from the beginning.

FIG. 5a) The result after 14 days of treatment with the claimed preparation.(Right hands (Hö) bottom pictures).

FIG. 5b) The result after 14 days of treatment with a potent corticosteroid (group III) Celastona valerat. (Left hand bottom picture.)

Figure 6A:
Figure 6B:

FIGS. 6a–6b

Tylotic eczema

Chronic eczema in both palms of the hands. Heredity of psoriasis.

FIG. 6a) The right hand (marked with H) was treated with the claimed preparation. The left hand was treated with a potent corticosteroid in combination with salicylic acid (Diprosalic ointment).

FIG. 6b) The treatment results after one month. Somewhat better results in the right hand palm after treatment.

Figure 7A:
Figure 7B:
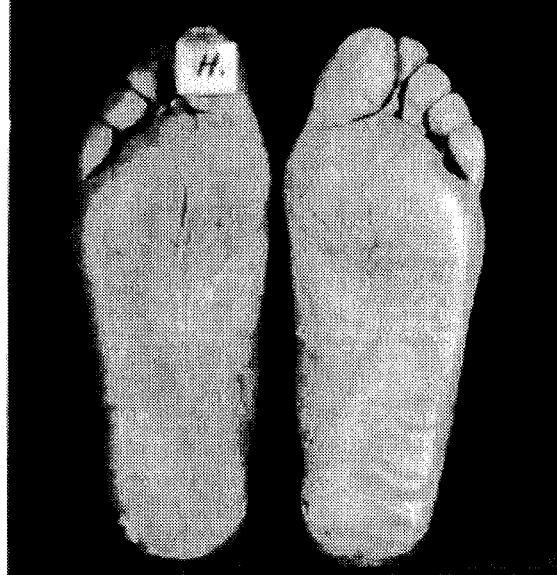
Figure 7C:
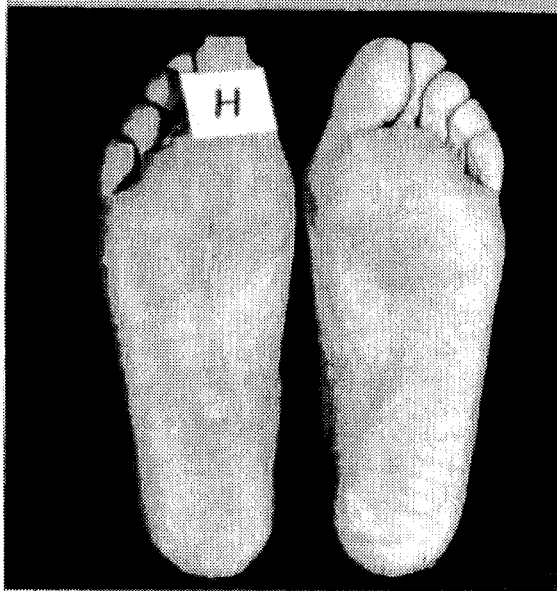

FIGS. 7a–7c

Nickel eczema, psoriasis, Hyperkeratosis, Rhagades

FIG. 7a) A woman with chronic nickel eczema and psoriasis for several years. Thick hyperkeratotis with rhagades in both soles of the feet. Worse at the right side, more pain when walking. The right foot was treated with the preparation of the present invention, the left foot was simultaneously treated with a potent steroid ointment (group III) Betnovat in combination with salicylic Essex cream. (The right side marked with H).

FIG. 7b) The results after hardly one month of treatment.

FIG. 7c) The result after slightly more than two months of treatment. The right side is remarkably better. Only a fold of the skin now remains of the deep, painful chapped formation. The pain has disappeared from the right foot.

Figure 8A:
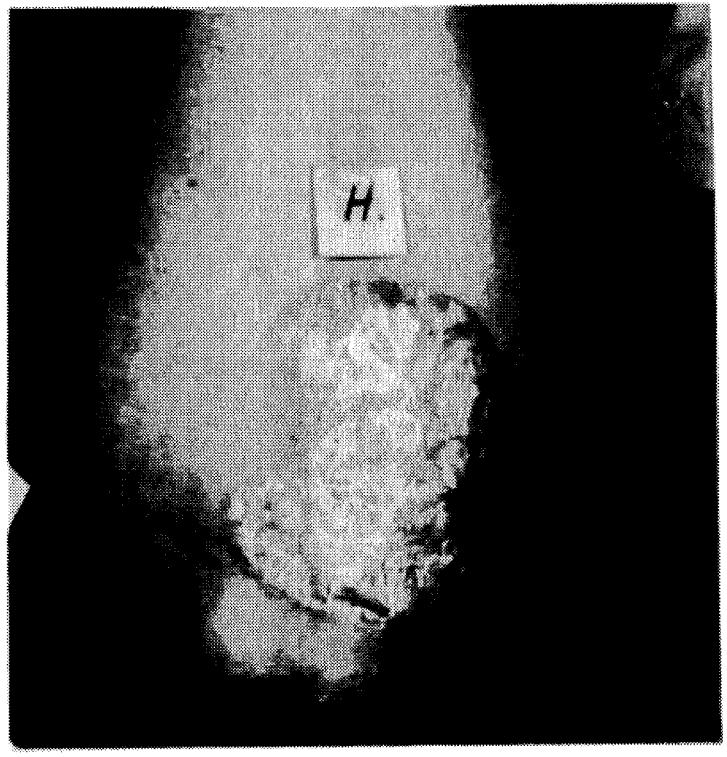
Figure 8A:
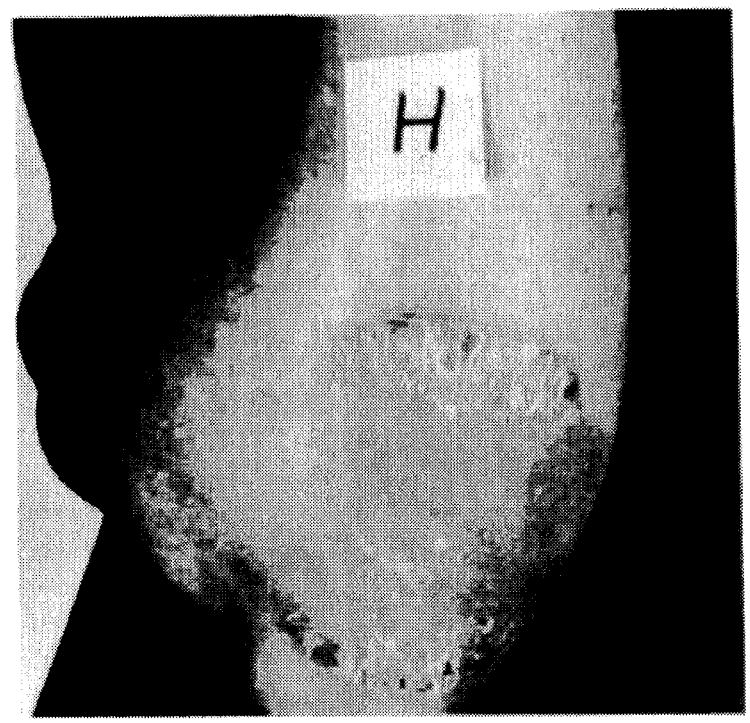
Figure 8B:
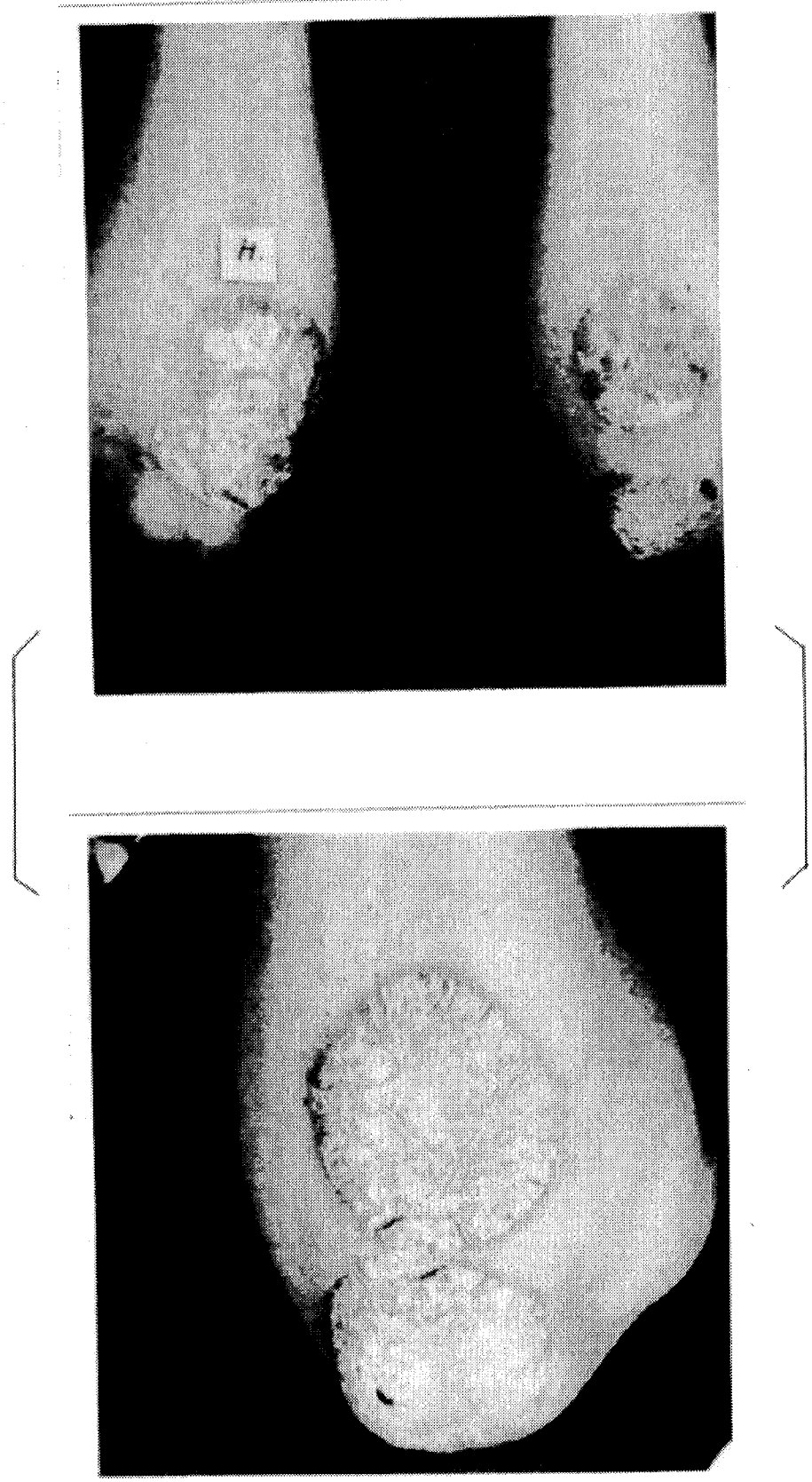
Figure 9:
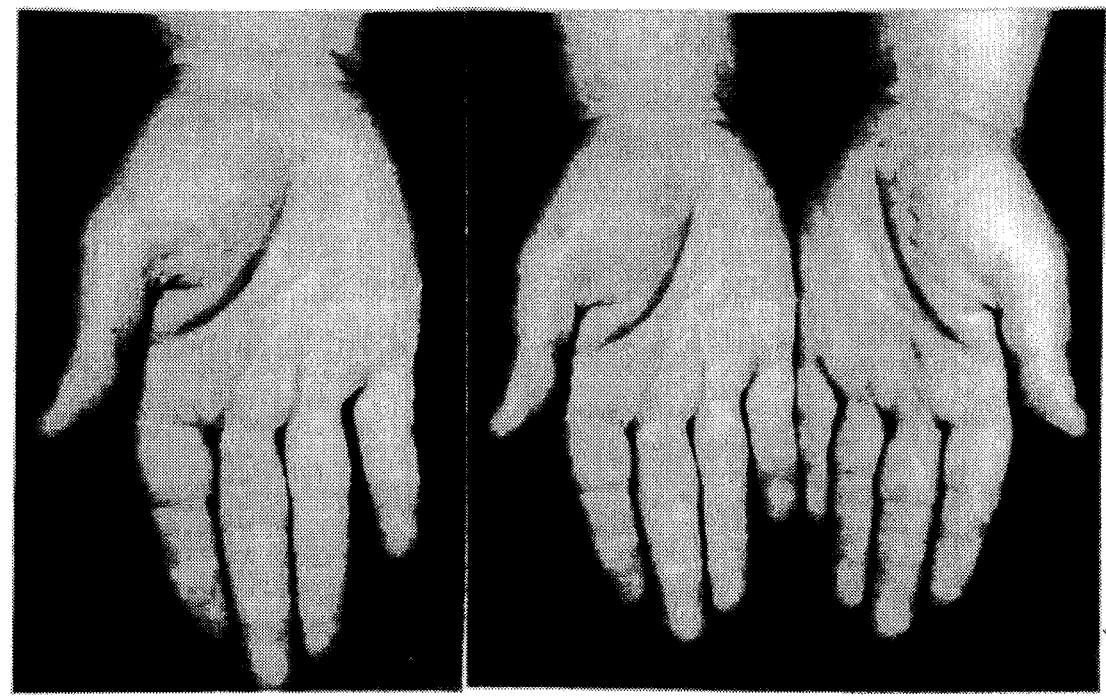
Figure 9:
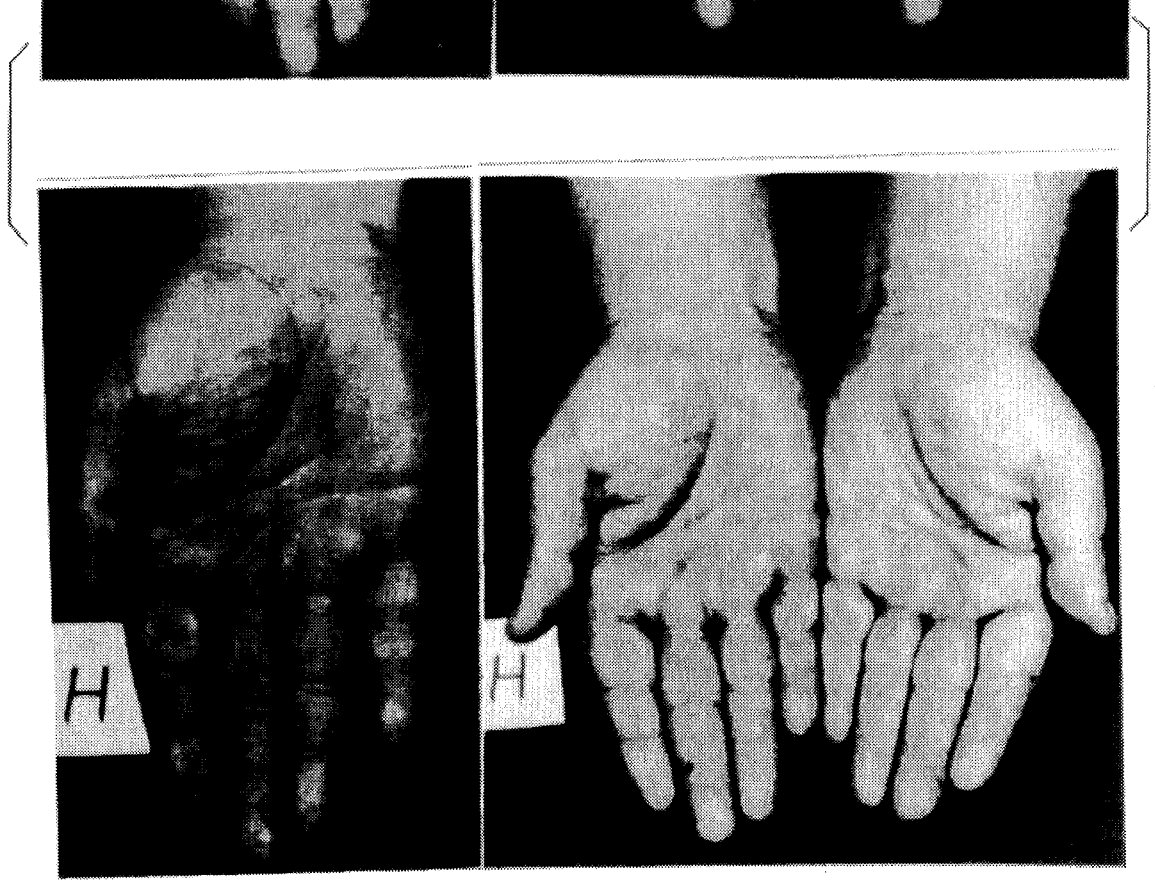

FIGS. 8a–8b

Psoriasis

A patient with psoriasis since 1967.

The right side (marked with H) is treated with the preparation of the present invention. The left hand side (not marked) was treated with a potent steroid ointment (group III) in combination with salicylic (Diprosalic). In combination, a further keratolytic treatment on the left hand side with salicylic Diachylon 5%.

FIG. 8a) The results after 14 days of treatment with the claimed preparation. The skin in the center is healed.

FIG. 8b) The results after 14 days of treatment with Diprosalic and salicylic Diachylon.

FIG. 9

Tinea Man (fungus infection)

A chronic fungus infection in the palm of the right hand caused by Trichophyton rubrum.
A. result after one month of treatment.
B. palm of the right hand was healed at that time.

I claim:

1. A method for treating skin and nails for conditions selected from the group consisting of hyperkeratotic skin diseases, psoriasis, seborrheic eczema, tylotic eczema, mycosis of the skin and nails, chronic onychia, pustulosis palmoplantaris, verrucae, hyperkeratosis, rhagades, clavi and discolored and thickened nails consisting essentially of applying to the affected area an effective amount of a composition consisting essentially of:

from 40 to 80% by weight of propylene glycol;

from 5 to 20% urea;

in a pharmaceutically acceptable carrier.

2. The method according to claim 1 wherein the composition contains from 50–80% by weight of propylene glycol.

3. The method according to claim 1 wherein the composition consists essentially of 20% urea and 80% propylene glycol.

4. The method according to claim 1 wherein the pharmaceutically acceptable carrier is ethanol.

5. The method according to claim 4 wherein the composition consists essentially of 20% urea, 40% propylene glycol, and 40% ethanol.

6. A method for treating skin and nails for conditions selected from the group consisting of hyperkeratotic skin diseases, psoriasis, seborrheic eczema, tylotic eczema, mycosis of the skin and nails chronic onychia, pustulosis palmoplantaris, verrucae, hyperkeratosis, rhagades, clavi and discolored and thickened nails consisting essentially of applying to the affected area an effective amount of a composition consisting essentially of:

from 40 to 80% by weight of propylene glycol;

from 5 to 20% urea;

up to 20% lactic acid;

in a pharmaceutically acceptable carrier.

7. The method according to claim 6 wherein the composition consists essentially of 20% urea, 10% lactic acid and 70% propylene glycol.

8. The method according to claim 6 wherein the pharmaceutically acceptable carrier is ethanol.

9. The method according to claim 6 wherein the composition consists essentially of 20% by weight urea, 40% by weight propylene glycol, 10% by weight lactic acid, and from 30–70% by weight ethanol.

10. The method according to claim 8 wherein the composition consists essentially of 15% urea, 40% propylene glycol, 10% lactic acid and from 30–70% ethanol.

11. A method for treating hyperkeratotic skin and nails for conditions selected from the group consisting of hyperkeratotic skin diseases, seborrheic eczema, tylotic eczema, psoriasis, mycosis of the skin and nails, chronic onychia, pustulosis palmoplantaris, verrucae, hyperkeratosis, rhagades, clavi and discolored and thickened nails consisting essentially of applying to the affected area of the skin or nails an effective amount of a composition consisting essentially of:

from 40 to 80% by weight of a mixture of propylene glycol and polyethylene glycol wherein the mixture contains at least 40% propylene glycol;

from 5 to 20% urea;

in a pharmaceutically acceptable carrier.

12. The method according to claim 11 wherein the pharmaceutically acceptable carrier is ethanol.

* * * * *